US00PP23560P3

(12) United States Plant Patent
Dirr

(10) Patent No.: US PP23,560 P3
(45) Date of Patent: Apr. 23, 2013

(54) CRAPEMYRTLE PLANT NAMED 'GAMAD IX'

(50) Latin Name: ***Lagerstroemia* hybrid**
Varietal Denomination: GAMAD IX

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 26 days.

(21) Appl. No.: 12/932,043

(22) Filed: Feb. 16, 2011

(65) Prior Publication Data

US 2012/0210479 P1 Aug. 16, 2012

(51) Int. Cl.
*A01H 5/00* (2006.01)

(52) U.S. Cl. ..... Plt./252

(58) Field of Classification Search ..... Plt./252
See application file for complete search history.

*Primary Examiner* — June Hwu

(74) *Attorney, Agent, or Firm* — David Wright Tremaine LLP

(57) ABSTRACT

A new and distinct cultivar of crapemyrtle, 'GAMAD IX', is provided. 'GAMAD IX' is a *Lagerstroemia indica*×*Lagerstroemia fauriei* hybrid, which is characterized by intermediate growth habit, mildew resistance, and earlier flowering with abundant purple flowers.

2 Drawing Sheets

Latin name of the genus and species of the plant claimed: 'GAMAD IX' is a crapemyrtle plant that is a *Lagerstroemia* hybrid.

Variety denomination: The new crapemyrtle plant claimed is of the variety denominated 'GAMAD IX'.

BACKGROUND OF THE INVENTION

The present invention relates to the discovery of a new and distinct cultivar of the ornamental flowering shrub *Lagerstroemia indica*×*Lagerstroemia fauriei*, commonly known as crapemyrtle, and hereafter referred to by the varietal denomination 'GAMAD IX', as herein described and illustrated.

The new crapemyrtle originated from open-pollinated seed of an unpatented seedling derived from 'Pocomoke'. 'GAMAD IX' was derived from plants grown at Dearing, Ga. from these seeds. The seedlings were planted in containers and selections were made for plants based on the following criteria: 1) intermediate growth habit; 2) mildew resistance; 3) early flowering; and 4) flower color and quality. 'GAMAD IX' was selected in 2004.

Asexual reproduction by traditional vegetative cuttings since 2004 at Dearing, Ga. and in Athens, Ga. has shown that the distinguishing characteristics of this new crapemyrtle variety 'GAMAD IX' are stable and reproduced true-to-type in successive generations.

SUMMARY OF THE INVENTION

The new crapemyrtle plant variety 'GAMAD IX' has not been observed under all possible environmental conditions. The phenotype may vary somewhat with variations in environment and cultural practices such as temperature and light intensity without, however, any variance in genotype.

The following traits have been repeatedly observed at Dearing, Ga. and Athens, Ga., and are determined to be unique characteristics of the new crapemyrtle plant variety 'GAMAD IX':

1. Intermediate size
2. Mildew resistance

3. Earlier flowering in mid to late June (USDA Zone 7)
4. Abundant red-purple N74B flowers There were no intermediate red-purple flowering varieties of crapemyrtle available for comparison. 'GAMAD IX' is similar in color to 'Catawba' (unpatented), but has a much smaller overall habit and is earlier flowering with abundant red-purple N74B flowers. The parent differs from 'GAMAD IX' by being more compact in habit and by having a deep pink to rose flower color.

BRIEF DESCRIPTION OF THE DRAWINGS

The accompanying photographic illustrations show typical 8-year-old specimens in full bloom of the new variety 'GAMAD IX'. The colors are as nearly true as is reasonably possible in a color representation of this type.

BOTANICAL DESCRIPTION

Figure 1:
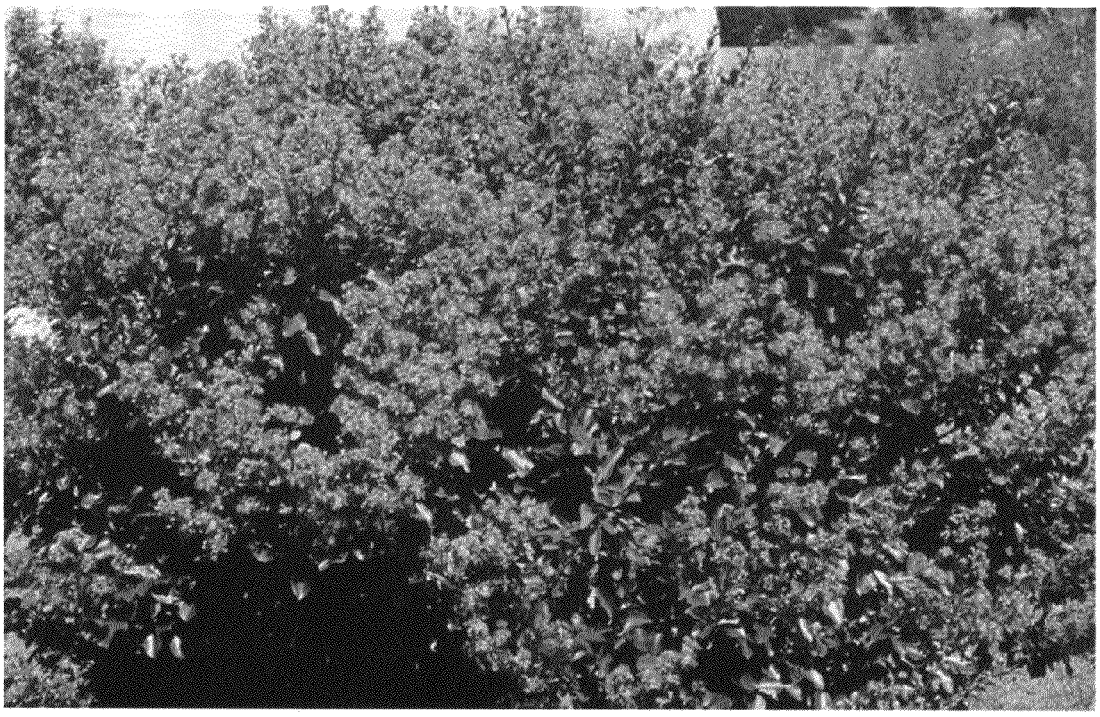
FIG. 1 is a photograph of the new variety 'GAMAD IX'.
Figure 2:
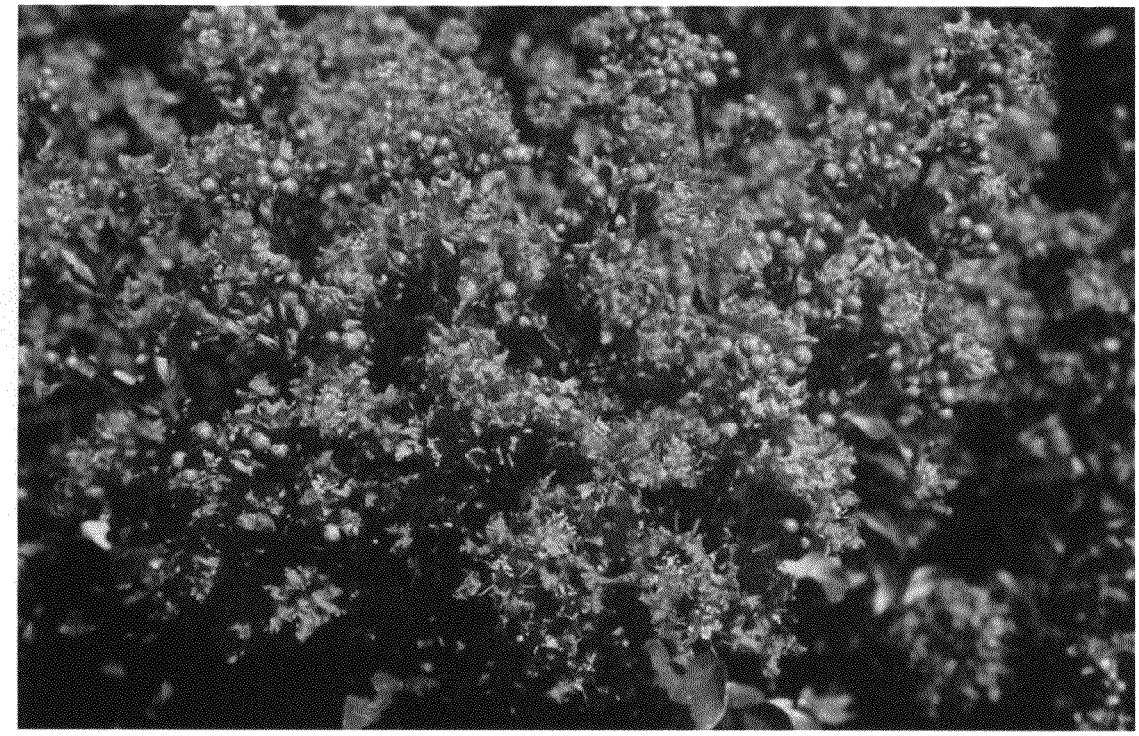
FIG. 2 is a photograph more closely illustrating the flowers of the new variety 'GAMAD IX'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and horticultural characteristics of the new variety 'GAMAD IX'. Where dimensions, sizes, colors, and other characteristics are given, it is to be understood that such characteristics are approximations and averages set forth as accurately as practicable. The descriptions reported herein are from specimen plants grown at Athens, Ga. Data were obtained in summer 2010 on plants that were 4 years old.

PLANT

Habit: Intermediate, rounded to broad-rounded.

Size:

*Height.*—140 cm.

*Width.*—180 cm.

Texture: Medium.

STEMS

Color: Greyed-brown N199B in first year changing to brown RHS 200C in the second year. No color designation was noted after the second year of growth.
Diameter: 2 mm.
Pubescence: Observed along edges.
Exfoliation: Strips.
Shape: Round.
Pith:
*Type*.—Solid.
*Diameter*.—1 mm.
*Color*.—Green RHS 137A.
Odor (of bruised stem): None.
Lenticels: None.
Internode length: 4.5 mm to 21 mm.

VEGETATIVE BUDS

Arrangement: Sub-opposite to alternate.
Type: Imbricate, ovoid to rounded.
Size:
*Length*.—3 mm.
*Width*.—1 mm.
Scale number: 3.
Scale color: Greyed-brown RHS 199D.
Position/disposition: 30 degrees to stem.
Number at node: 1.
Pubescence: None.
Shape: Ovoid to rounded.

LEAF SCAR

Shape: Raised half ellipse.
Vascular bundle traces: None observed.
Pubescence: None.
Position of bud: Directly on top.
Color differentiation: Green RHS 137A.
Size:
*Height*.—1 mm.
*Width*.—2 mm.

TRUNK OR LARGE STEMS

Color: Grey-brown RHS 199C.
Size of stem on which exfoliation begins: 14 mm, with some peeling occurring.
Diameter: 14 to 19 mm.
Texture: Slightly exfoliating. No color difference was noted between the color of the trunk once exfoliated and the color of the unexfoliated trunk (199C).

LEAF

Color at emergence:
*Upper*.—Yellow-green RHS 148A.
*Lower*.—Yellow-green RHS 148B.
Color during summer season:
*Upper*.—Dark-green RHS 136A.
*Lower*.—Green RHS 138A.
Color during fall season: No appreciable color was noted for fall foliage.
Mature size:
*Length*.—50 mm (on average).
*Width*.—32 mm (on average).
Apex: Acuminate.
Base: Acute.
Margin: Entire, undulating.
Shape: Obovate.
Vein color: Yellow-green RHS 146D.
Pubescence: Finely hairy on entire upper leaf surface, only observed along veins and midrib on lower surface.
Arrangement on stem: Sub-opposite to alternate.
Venation: Pinnate.
Texture: Leathery.
*Thickness*.—0.5 mm thick.
*Degree of waxiness of surfaces*.—Moderately waxy.

PETIOLE

Length: 2 mm.
Shape: Mostly rounded to semi-oval.
Color: Grey-purple RHS 187B on top and Yellow-green RHS 146D underneath.
Pubescence: Finely hairy.
Diameter: 1 mm.

FLOWER BUDS

Size:
*Length*.—7 mm.
*Width*.—5.5 mm.
Color: Greyed-red RHS 178A.
Shape: Oval-rounded.
Pubescence: None.
Time of full maturity: Mid to late June.
Time range for showiness: Approximately 9 to 11 weeks for buds and flowers.

FLOWER

Inflorescences:
*Type*.—Paniculate.
*Size*.—Length: 9.25 cm. Width: 7.5 cm.
*Flower type*.—Single solitary, held in a paniculata inflorescence.
*Average number of flowers per inflorescence*.—100-150.
*Average flower size*.—¾"-1½".
*Color at emergence*.—Red-purple N74B.
*Color at full bloom*.—Red-purple N74B.
*Color at fading*.—Purple RHS N79A.
*Peduncle*.—Color: Greyed-purple RHS 183C. Pubescence: Finely hairy along edges. Average length: 5"-6".
Petals:
*Number*.—6.
*Size*.—Length: 21 mm. Width: 15 mm.
*Shape*.—Fan-shaped.
*Apex*.—Ruffled, rounded.
*Base*.—Sagittate.
*Margin*.—Ruffled.
*Pubescence*.—None.
*Texture*.—Smooth.
*Color at peak of bloom*.—Upper surface: Red-purple N74B. Lower surface: Red-purple N74B.
*Pedicels*.—Color: Greyed-purple RHS 185A. Pubescence: None. Average length: ½"-¾".
Sepals: A botanical description of the sepal is not available.

MALE REPRODUCTIVE STRUCTURES

*Number.*—6 (fertile); 20 to 30 (sterile).
*Pollen color*.—Yellow-orange RHS 14A.
*Pubescence*.—None.

Anther:
*Size*.—(Both fertile and sterile). Length: 1.5 mm. Width: 1 mm.
*Color*.—Yellow-green RHS 144A (fertile); Yellow-orange RHS 14A (sterile).

Filament:
*Size.*—8 mm to 12 mm (fertile); 8 mm to 10 mm (sterile).
*Color*.—Red-purple RHS 60B (fertile); Red-purple RHS 69B (sterile).

FEMALE REPRODUCTIVE STRUCTURES

Pistil:
*Size*.—Length: 16 mm. Width: 0.5 mm.
*Position*.—Superior.
*Pubescence*.—None.

Stigma:
*Shape*.—Rounded.
*Color*.—Yellow-green RHS 148A.
*Pubescence*.—None.

Style:
*Length.*—16 mm.
*Shape*.—Linear.
*Color*.—Red RHS 46A.
*Pubescence*.—None.

Ovary:
*Shape*.—Oval to round.
*Number*.—One per flower.
*Pubescence*.—None.
*Size* (*diameter*).—2 mm.
*Color*.—Yellow RHS 3C.

FRUIT

*Type*.—Dehiscent, six-valved capsule.
*Size*.—Length: 9 mm. Width: 6 mm to 7 mm.
*Color during ripening*.—Early: Greyed-orange RHS 165B at tip; Yellow-green RHS 146C at base. Mid: Yellow-green RHS 146B. Late: Brown RHS 200B (before splitting); Greyed-orange RHS 165A (after seed dispersal).
*Shape*.—Broad-ellipsoidal.
*Number per infructescence.*—80 to 90.
*Pubescence*.—None.
*Number of carpels.*—6.
*Persistence* (*effective period*).—3 months holding into winter.

SEED

Shape: Oval-rounded.
Size: Length: 5 mm. Width: 2 mm.
Color: Brown RHS 200B (seed); about Greyed-orange RHS 164C (wing).
Number per fruit: 15 to 30.
Pubescence: None.

PLANT DISEASE AND PEST RESISTANCE/SUSCEPTIBILITY

Resistance: Mildew and *Cercospora*. No further information regarding plant disease and/or pest resistance/susceptibility is available.

What is claimed is:

1. A new and distinct variety of crapemyrtle plant named 'GAMAD IX', substantially as illustrated and described herein.

* * * * *